(12) United States Patent
Garrigue

(10) Patent No.: US 9,919,089 B2
(45) Date of Patent: Mar. 20, 2018

(54) SELF-CONTAINED HEART PUMP, AND METHOD IMPLEMENTED IN SUCH A PUMP

(71) Applicant: FINEHEART, Bordeaux (FR)

(72) Inventor: Stephane Garrigue, Begles (FR)

(73) Assignee: FINEHEART, Bordeaux (FR)

( * ) Notice: Subject to any disclaimer, the term of this patent is extended or adjusted under 35 U.S.C. 154(b) by 0 days.

(21) Appl. No.: 14/859,798

(22) Filed: Sep. 21, 2015

(65) Prior Publication Data

US 2016/0008527 A1    Jan. 14, 2016

Related U.S. Application Data

(63) Continuation of application No. 13/016,188, filed on Jan. 28, 2011, now Pat. No. 9,138,517.

(30) Foreign Application Priority Data

Jan. 28, 2010   (FR) ...................................... 10 50557
Dec. 30, 2010   (WO) ................. PCT/FR2010/052940

(51) Int. Cl.
*A61N 1/362*   (2006.01)
*A61M 1/12*    (2006.01)
(Continued)

(52) U.S. Cl.
CPC ............ *A61M 1/122* (2014.02); *A61M 1/125* (2014.02); *A61M 1/127* (2013.01); *A61N 1/365* (2013.01); *A61M 1/101* (2013.01); *A61M 1/1005* (2014.02); *A61M 1/1086* (2013.01); *A61M 1/12* (2013.01); *A61M 2205/054* (2013.01); *A61M 2205/33* (2013.01); *A61M 2205/3303* (2013.01); *A61M 2205/3334* (2013.01);
(Continued)

(58) Field of Classification Search
None
See application file for complete search history.

(56) References Cited

U.S. PATENT DOCUMENTS 5,147,388 A *  9/1992  Yamazaki ............. A61M 1/101
                                                    600/16
5,507,629 A    4/1996  Jarvik
(Continued)

FOREIGN PATENT DOCUMENTS

EP    0 764 448    3/1997
EP    1 129 736    9/2001
(Continued)

*Primary Examiner* — Christopher D Koharski
*Assistant Examiner* — Elizabeth K So
(74) *Attorney, Agent, or Firm* — Young & Thompson

(57) ABSTRACT

A heart pump includes a rotative impeller partly inserted into the systemic ventricle, this rotative impeller being equipped with a membrane sutured to the outer wall of the heart in such a way as to secure the rotative impeller to the wall of the heart, a housing arranged inside the systemic ventricle in such a way as to draw up then discharge blood, a motor connected to the housing and arranged partly outside the systemic ventricle in such a way as to facilitate maintenance; an integrated management unit in the epigastric region including a power supply and a rotative impeller control unit; and a wired link between the management unit and the rotative impeller.

20 Claims, 2 Drawing Sheets

(51) Int. Cl.
*A61N 1/365* (2006.01)
*A61N 1/375* (2006.01)
*A61M 1/10* (2006.01)
*A61N 1/39* (2006.01)
*A61N 1/372* (2006.01)

(52) U.S. Cl.
CPC ............... *A61M 2205/3523* (2013.01); *A61M 2205/8206* (2013.01); *A61M 2210/125* (2013.01); *A61M 2230/04* (2013.01); *A61N 1/362* (2013.01); *A61N 1/375* (2013.01); *A61N 1/37288* (2013.01); *A61N 1/39* (2013.01); *A61N 1/3962* (2013.01)

(56) References Cited

U.S. PATENT DOCUMENTS

| | | |
|---|---|---|
| 5,888,241 A | 3/1999 | Jarvik |
| 6,135,729 A | 10/2000 | Aber |
| 6,217,541 B1 | 4/2001 | Yu |
| 6,234,772 B1 | 5/2001 | Wampler et al. |
| 6,406,422 B1 | 6/2002 | Landesberg |
| 7,022,100 B1 | 4/2006 | Aboul-Hosn et al. |
| 8,409,276 B2 | 4/2013 | Wampler |
| 2005/0107657 A1 | 5/2005 | Carrier et al. |
| 2006/0036127 A1 | 2/2006 | Delgado |
| 2008/0004485 A1 | 1/2008 | Moreschi |
| 2009/0024212 A1 | 1/2009 | Siess et al. |
| 2011/0144413 A1 | 6/2011 | Foster |
| 2011/0184224 A1 | 7/2011 | Garrigue |

FOREIGN PATENT DOCUMENTS

| | | |
|---|---|---|
| WO | 99/34847 | 7/1999 |
| WO | 00/44417 | 8/2000 |
| WO | 2004/101029 | 11/2004 |
| WO | 2010/010407 | 1/2010 |
| WO | 2011/092394 | 8/2011 |

\* cited by examiner

SELF-CONTAINED HEART PUMP, AND METHOD IMPLEMENTED IN SUCH A PUMP

FIELD OF THE INVENTION

The present invention relates to an artificial heart pump allowing for the regulation of blood flow.

BACKGROUND OF THE INVENTION

The heart is a hollow muscle that, through its rhythmical contraction, ensures the progress of blood through the vessels. It comprises four cavities. The right atrium and the left atrium arranged in the upper part of the heart; the right ventricle and the left ventricle arranged in the lower part.

The right ventricle is designed to receive blood coming from the right atrium and then eject it into the pulmonary artery. This forms a "lesser circuit" allowing for the blood to be sent to the lungs for reoxygenation.

The left ventricle retrieves the oxygenated blood from the lungs via the left atrium and then ejects it towards the aorta to bring oxygen to all of the tissues of the organism. This is the "greater circulation", called systemic circulation.

Cardiac insufficiency (CI), the progressive inability of the heart to provide the blood flow necessary for an individual's metabolic needs during everyday life, is the second biggest cause of death in Western countries. The treatment of cardiac insufficiency, which consists of increasing the blood flow in a manner appropriate to the patient's needs, is not very effective with current techniques, and is extremely costly.

Document US2009/0024212 is known, describing a pump for the treatment of cardiac insufficiency due to the inactivity of the sigmoid valves of the heart. This pump has an elongated shape extending from the inside of the left ventricle to the inside of the aorta in such a way as to replace the function of the valves.

Document U.S. Pat. No. 6,217,541 is also known, describing a heart pump that is also inserted through the aorta to the inside of the ventricle. The end of the pump draws up the blood contained in the left ventricle and then transfers it to the aorta via a flexible channel integral with the end of the pump and arranged through the valves.

The pumps described above require complex installation, and are not designed for permanent use.

Document U.S. Pat. No. 6,234,772 is also known, describing an implantable rotary pump. This pump is magnetically driven and is used to force blood circulation, avoiding any stagnant zones. This document remains silent with regard to any efficient installation of the pump.

Document WO2010/010407 describes a rotary heart assist pump discharging the blood from the left ventricle through the aortic valve. This pump is fixed through the aortic valve with fasteners in the aorta and at the ventricular apex. The electric motor is located in the conduit passing through the aortic valve.

Finally, document US2005/0107657 is known, describing a left ventricular assist device (mixed-flow blood pump) with a so-called "radial" blood inlet circuit and a so-called "axial" blood outlet circuit by means of a rotative impeller located at the centre of the device. The base is held inside the left ventricular cavity by a semi-rigid rod through the apex of the ventricle, while the summit of the device passes through the aortic valve with functional modification or elimination of the valve. Surgically, a sternotomy with installation of a cardiopulmonary bypass is necessary, as an incision must be made in the aortic root. The electric motor is located inside the device, therefore inside the left ventricle. This document also discloses an optimum efficiency equation between the diameter of the pump and the number of revolutions per minute of the impeller (up to 11,000 rpm). The diameter of the pump is given as ~20-22 mm.

SUMMARY OF THE INVENTION

The purpose of the present invention is a new heart pump that is easy to install compared with the installation of current systems.

Another purpose of the invention is simplicity in the maintenance of such a pump, which is designed for long-term use.

A further purpose of the invention is a pump that is not very invasive in the ventricle of the heart and offers stability in keeping stable.

At least one of the aforementioned aims is achieved with a heart pump comprising:
- an impeller inserted partly in the systemic ventricle of a heart, through the wall of the heart, this impeller being equipped with:
  - a sealing and fixing membrane that is sutured to the outer wall of the heart, the epicardium, in such a way as to secure the impeller to the wall of the heart,
  - a housing arranged inside the systemic ventricle in such a way as to draw up then discharge the blood in the direction of sigmoid valves of the systemic ventricle,
  - a motor arranged partly outside the systemic ventricle and connected to the housing;
- a management unit comprising a power supply and an impeller control unit;
- a wired link between the management unit and the impeller.

By systemic ventricle is meant the ventricle dedicated to blood circulation to supply a patient's body with oxygen via the aorta. In principle, this role falls to the left ventricle, but in certain pathological situations, this role can be played by the right ventricle.

With the heart pump according to the invention, the impeller is securely fixed to the wall of the heart and the patient can move actively without any risk of lesions. The blood flow is acted upon directly by directly controlling blood circulation. The present pump is aimed at all cardiac insufficiency patients without prerequisite criteria.

Furthermore, the arrangement of the motor partly outside the heart means that the motor is accessible from the outside of the ventricle, which allows for simplified maintenance.

Advantageously, the impeller can be inserted and sutured to the bottom part of the heart near the apex of the heart. Preferably, the motor is removable so that it can easily be replaced in the event that it fails.

The impeller according to the invention is a biocompatible impeller of different types, for example rotative or discharge.

According to a first variant of the invention, the impeller is of a rotative type and comprises a propeller shaft arranged in the housing. In this case, blood discharge takes place by centrifugal force. The second variant can be characterised by the fact that the impeller is of the rotative type and comprises an Archimedes screw or "worm" shaft arranged in the housing. In this case, discharge takes place by longitudinal thrust along the housing.

Preferably, the housing is a longilinear cylinder the side wall of which is perforated in such a way as to enable the discharge of the blood drawn up, and the axis of rotation of which is facing corresponding sigmoid valves. Such an arrangement allows for the blood to be ejected towards sigmoid valves, but also allows for the blood coming from the systemic atrium to be efficiently drawn up. By systemic atrium is meant the atrium associated with the systemic ventricle.

According to the invention, the management unit can be arranged outside the patient, but it is preferably internal, and advantageously in the epigastric region, in the upper part of the abdomen. Thus, unlike systems of the prior art, the power supply according to the invention is preferably implanted in its entirety without any externalisation. To achieve this, the power supply can comprise at least one battery, and preferably a rechargeable battery; the recharging of the battery can optionally take place by percutaneous transduction.

The pump according to the invention can thus be completely implanted and self-contained.

According to an advantageous characteristic of the invention, the pump can also comprise a sensor, called an activity sensor, to collect cardiac activity in such a way as to synchronise the operation of the impeller with the electrosystolic activity of the heart; this activity sensor can be connected to the wall of the heart and can have a wired link to the management unit. This configuration allows for the operation of the impeller to be synchronised with the heart rhythm.

In a fully integrated configuration, the activity sensor is connected to the management unit via said wired link. In this case, the wired link forms the only link between the management unit and the impeller.

According to an advantageous embodiment of the invention, the heart pump comprises a cardiac activity collection and stimulation sensor, called the systemic sensor, connected to the wall of the systemic ventricle and capable of communicating with the management unit via a wired or wireless link, by wireless telemetry in particular. This sensor plays a dual role of collecting heart information and stimulating the heart to contract the muscle in response to an instruction coming from the management unit. A second sensor of the same type, known as the non-systemic sensor, can be provided, connected to the wall of the non-systemic ventricle and capable of communicating with the management unit via a wired or wireless link, by wireless telemetry in particular. In this case, the two sensors can be controlled to perform biventricular stimulation. The fact of being able to stimulate the heart allows for the combining of a direct action of the impeller on blood flow and an indirect action of heart contraction. The heart rhythm detected by different sensors also allows for the operation of the impeller to be synchronised with cardiac activity. In other words, the impeller is synchronised with the ventricular systolic activity when it is possible to collect information about cardiac activity, or it can operate in continuous mode.

Another cardiac activity collection and stimulation sensor can also be envisaged, called the atrium sensor, connected to the wall of the systemic atrium and capable of communicating with the management unit in such a way as to complete the cardiac activity collection and stimulation system. Communication can be wired or wireless, by wireless telemetry in particular.

A sensor is self-contained with regard to power when it communicates wirelessly with the management unit.

In addition in particular to the above, the pump according to the invention can advantageously comprise a cardiac activity collection, stimulation and defibrillation sensor, called the defibrillation sensor, connected to the wall of the heart and having a wired link to the management unit; the control unit is also configured as a defibrillator.

Alternatively, a management unit with a wireless connection to a defibrillator can be provided. The defibrillator can be external (cutaneous) or not, in particular an independent implantable automatic defibrillator, but communicating with the management unit by radio waves in particular.

According to an advantageous embodiment of the invention, a second impeller as described above is arranged on the non-systemic ventricle and is also connected to the management unit.

According to another aspect of the invention, a method is proposed to regulate blood flow in a heart by means of a heart pump as described above.

According to the invention, blood flow is regulated by controlling the speed and operating time of the pump on the basis of predetermined control laws or on the basis of an automatic control instruction relating to cardiac activity. With the automatic control instruction, blood flow is controlled in real time.

Advantageously, the automatic control instruction is developed by collecting cardiac activity by means of a sensor connected to the wall of the heart and having a wired link to the management unit. Blood flow can also be regulated by stimulating the heart by means of at least one stimulation sensor connected to the wall of the heart and having a wired link to the management unit.

BRIEF DESCRIPTION OF THE DRAWINGS

Further advantages and characteristics of the invention will become apparent on examining the detailed description of an embodiment, which is in no way limitative, and the attached drawings, in which.

DETAILED DESCRIPTION OF THE INVENTION

Although the invention is not limited thereto, a heart pump implanted in the left ventricle of a heart, which is in principle the systemic ventricle, will now be described. However, the invention can be applied in the same way to a right ventricle when this is the systemic ventricle.

Figure 1:
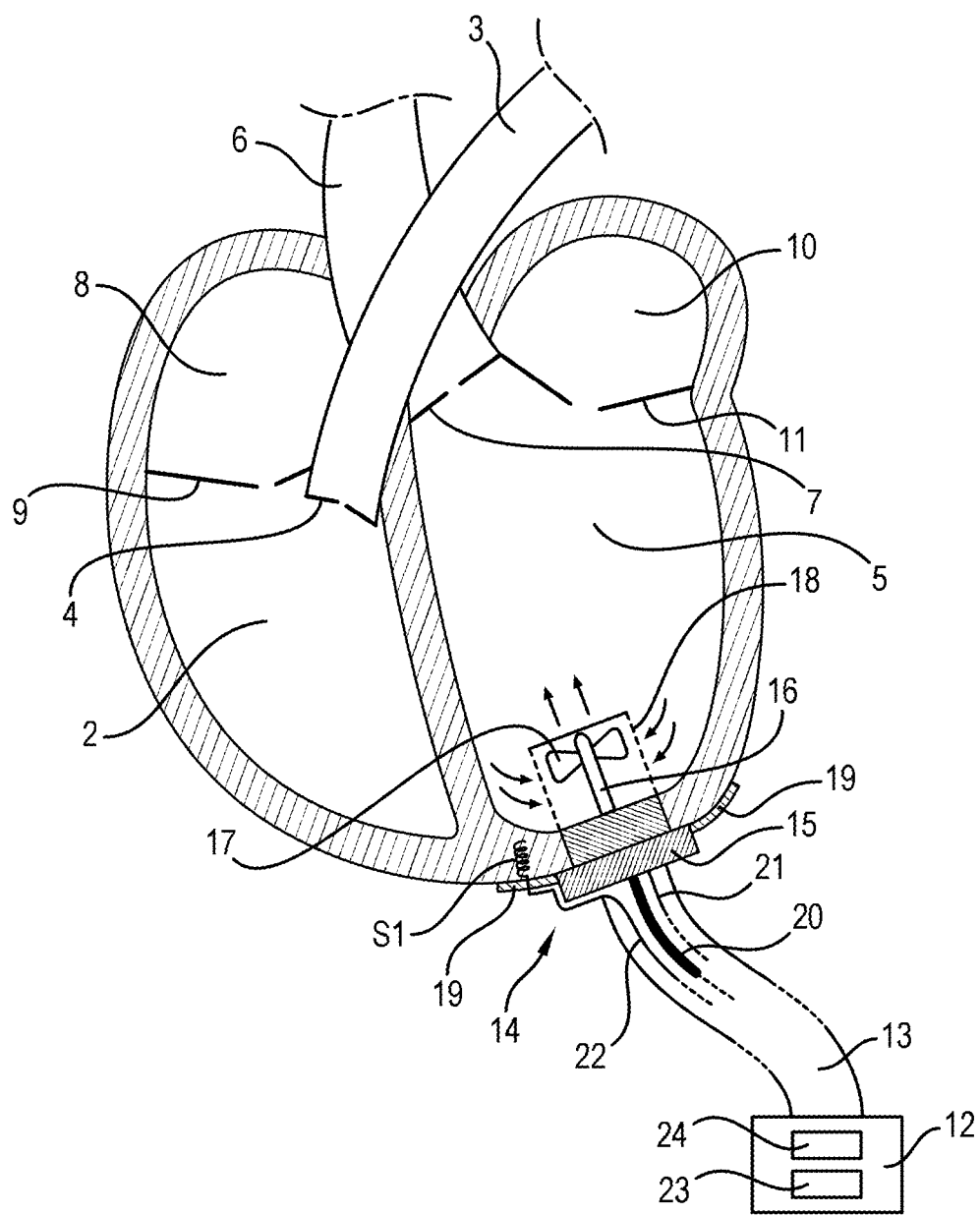
FIG. 1 is a simplified diagrammatic view of a heart pump according to the invention inserted into the left ventricle of a heart.
Figure 2:
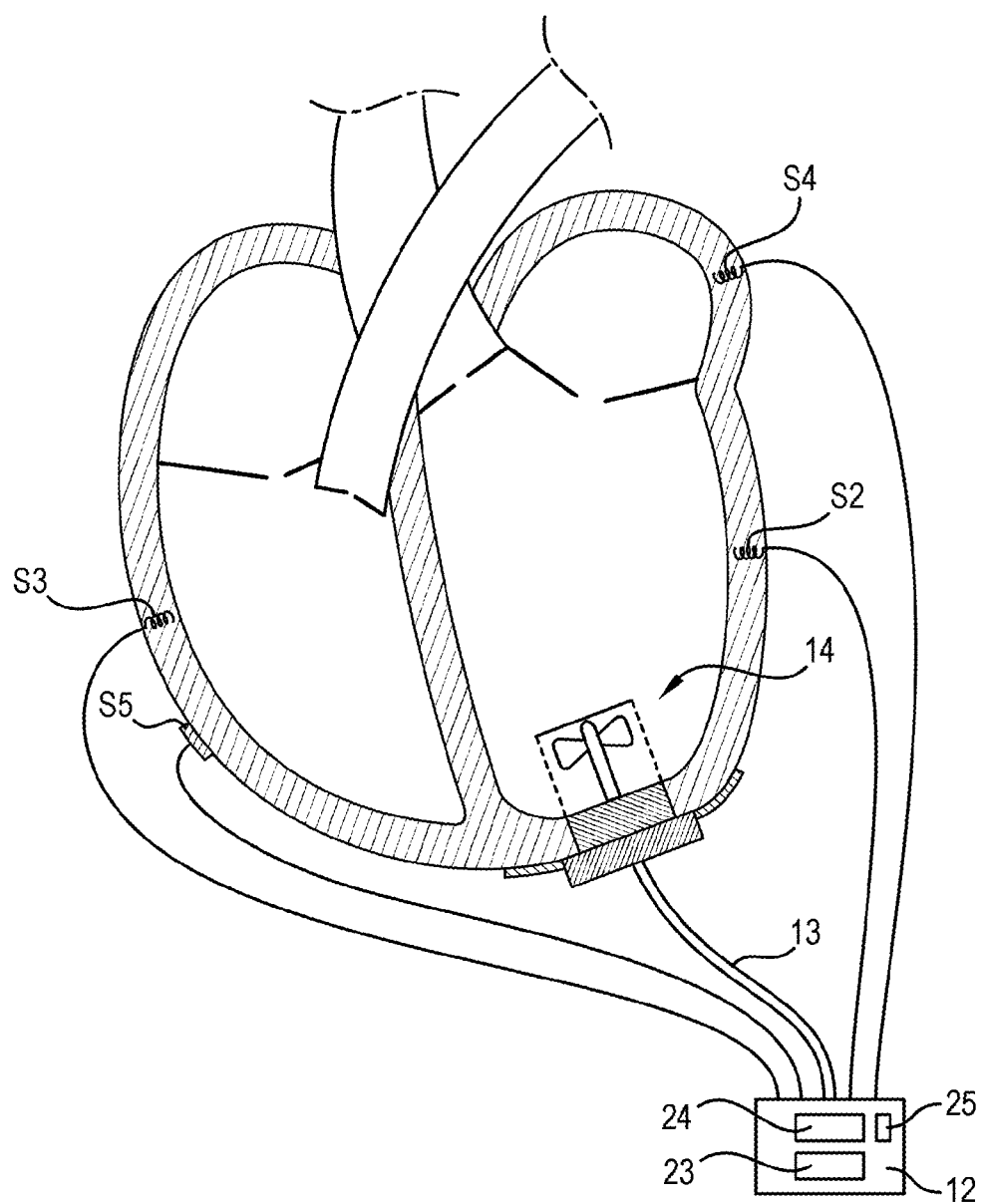
FIG. 2 is a diagrammatic view of a heart pump according to the invention equipped with a plurality of sensors or epicardial electrodes in such a way as to efficiently synchronise the heart pump relative to cardiac activity.

In FIGS. 1 and 2, the different components common to the various variants or embodiments have the same reference.

In FIGS. 1 and 2, the heart as a whole is designated by the reference 1. The right ventricle 2, which has the function of ejecting blood towards the pulmonary artery 3 through sigmoid valves 4 can be seen. The left ventricle 5 has the function of performing systemic circulation by ejecting the oxygenated blood towards the aorta 6 via sigmoid valves 7.

The right atrium 8 supplies the right ventricle 2 with blood via auriculo-pulmonary valves 9. The left atrium 10 supplies the left ventricle 5 with blood via auriculo-pulmonary valves 11.

The pump according to the invention comprises a management unit 12 having a wired link 13 to an impeller 14 inserted partly in the left ventricle 5, at the apex, that is, at the lower tip of the left ventricle.

The impeller comprises a motor 15 placed largely outside the left ventricle so that it is easily accessible following a minithoracotomy (surgical incision) and/or an operation by the epigastric route compared with a sternotomy, where the thorax is completely opened. This motor can be a magnetically driven motor equipped with a rotor extending to the inside the ventricle in the form of a drive shaft. The shaft can be a "worm" type (Archimedes screw) allowing for the blood to be ejected from the bottom of the ventricle towards the aorta 6. This shaft can advantageously be a drive shaft 16 with a propeller 17 arranged at its free end. This propeller is formed in such a way that the dynamics of the blood fluid allow for the blood to be ejected towards the aorta 6. To achieve this, a cylindrical housing 18 is formed all around the shaft 16 and its propeller 17. The housing 18 comprises at least one opening, preferably several openings in a honeycomb structure for example, on its side wall in such a way as to allow for the drawing up of blood coming from the left atrium and its discharge through the upper opening in the cylinder forming the housing 18 through the action of the propeller 17. The axis of rotation of the cylindrical housing 18 is directed towards the aortic orifice. Such an orientation is advantageously obtained during the positioning of the impeller by suturing. A person skilled in the art will easily understand that other types of miniaturised biocompatible motors can be used to draw up and discharge the blood. Generally, the materials used for the implementation of the pump according to the invention are biocompatible and can therefore be implanted in the patient's body.

The impeller 14 is inserted into the apex of the heart and is held there by means of a circular sealing and fixing membrane 19.

Other types of membrane providing a complete seal can be envisaged. This membrane 19 is sutured to the external wall of the heart all around the motor 15 in such a way as to ensure a complete seal between the left ventricle 5 and the outside of the heart.

The wired link 13 links the impeller 14 to the management unit 12, which comprises a power supply 23 such as a battery, and a remotely configurable control unit 24. The wired link 13 comprises a control line 21 enabling the control unit 24 to send control instructions to the impeller 14, and the control line 21 can be two-way. The cable 20 is a power supply cable to the motor 15. The cable 22 allows for the management unit 12 to be electrically connected to an optional activity sensor S1 inserted into the wall of the heart in such a way as to collect the cardiac activity of the heart. The activity sensor S1 can be inserted through the sealing and fixing membrane 19 or outside it in order not to damage the seal. It can also be capable of stimulating the left or right ventricle. In these cases, it is arranged in the wall corresponding to the left ventricle or the right ventricle.

With such a heart pump according to the invention, the link between the management unit 12 and the impeller 14 is obtained by the sole link 13.

During operation, the management unit is configured in such a way as to modulate the rotating speed and operating time of the motor as a function of predetermined laws or control instructions. When a sensor is provided to collect cardiac activity, for example the activity sensor S1, the control unit 24 can be configured to automatically control the motor based on the heart rhythm, in real time. This automatic control allows for the rotative impeller to be synchronised with the heart rate.

Preferably, the management unit is implanted in the epigastric region, inside the patient's abdomen. Provision can thus be made for the control unit 24 to be remotely configurable by wireless communication.

FIG. 2 shows an example of a heart pump according to the invention in an embodiment incorporating a number of sensors or epicardial electrodes.

The sensors arranged on the heart are of information collecting and stimulating types. They are used to identify the start of electrical activation and synchronise the impeller with the opening of the valves. When the two ventricles are each subject to one impeller, each impeller is synchronised with the opening of the corresponding valves. Advantageously, the frequency of each impeller is adapted in such a way as to deliver a systolic ejection volume of between 20 and 35 ml for each cardiac cycle.

Given that the activation of an impeller in a ventricle with an open valve (during systole) increases the quantity of blood ejected, the pump according to the invention allows for the systolic ejection volume, and consequently blood flow, to be increased.

According to the example shown in FIG. 2, the pump according to the invention comprises a cardiac activity collection and stimulation sensor, called the systemic sensor S2, allowing in particular for the left ventricle to be stimulated by muscular contraction. This systemic sensor S2, connected to the management unit 12, is arranged in the wall of the heart on the left ventricle. Similarly, another cardiac activity collection and stimulation sensor, called the non-systemic sensor S3, is arranged on the wall of the right ventricle and is connected to the management unit 12. It allows in particular for the right ventricle to be stimulated by muscular contraction. The combined action of the two sensors S2 and S3 allows for biventricular simulation to be performed from the control unit 24 in such a way as to maintain a heart rhythm according to a predetermined law or in response to given instructions.

In FIG. 2, a cardiac activity collection and stimulation sensor, called the atrium sensor S4, connected to the management unit 12, can also be seen on the wall of the left atrium. Advantageously, the control unit 24 can be configured to synchronise the stimulation of the systemic S2 and non-systemic S3 sensors relative to the information collected from this sensor S4.

In addition in particular to the above, each of the sensors S2 and S4 can play the role of the activity sensor S1.

In order to handle the risk of ventricular fibrillations, provision is made for an epicardial patch or defibrillation sensor S5 arranged on the outer wall of the heart, the control unit being configured to both detect a fibrillation situation and deliver low energy electrical pulses.

To fully comprehend cardiac activity, provision is made for a patient activity detector 25, such as an accelerometer or pressure sensor, arranged for example in the management unit 12 or incorporated into one of the aforementioned sensors. Such a detector can be useful for a patient with chronotropic incompetence in order to detect and signal any acceleration in the patient's physical activity to the control unit.

Provision is also made for a hemodynamic detector to detect the patient's hemodynamic status in such a way as to supplement the information obtained about the heart rhythm and control the impeller effectively. The hemodynamic detector can be an endocardial acceleration detector of PEA (Peak Endocardial Acceleration) type, implanted for example together with the electrode S2.

The heart pump according to the invention therefore allows for the blood flow to be regulated in order to avoid any cardiac insufficiency. Furthermore, it can be implanted in the heart by minithoracotomy. The rotative impeller can be inserted at the apex (the lower tip) of the left ventricle and if necessary a second rotative impeller can be inserted at the apex of the right ventricle. These two impellers can advantageously be connected to a management unit placed in the epigastric region. It is thus a closed system without externalisation of electrical and power supply equipment.

Of course, the invention is not limited to the examples that have just been described and numerous adjustments can be made to these examples without exceeding the scope of the invention.

The invention claimed is:

1. A heart pump configured to be inserted partly into a systemic ventricle of a heart, through a wall of the heart, the heart pump comprising:
    a housing configured to be positioned inside the systemic ventricle to draw up blood inside the systemic ventricle and to discharge the blood inside the systemic ventricle and through sigmoid valves of the systemic ventricle;
    an impeller configured to be inserted inside the housing;
    a motor connected to the housing;
    a sealing and fixing membrane fastened to and around the motor and configured to secure the heart pump to the wall of the heart and to partly arrange the motor outside the systemic ventricle;
    a management unit comprising a power supply, and an impeller control unit; and
    a wired link between the management unit and the impeller.

2. The heart pump according to claim 1, wherein the sealing and fixing membrane is circular thereby being configured to ensure a complete seal and secure the heart pump to the bottom part of the heart near an apex of the heart.

3. The heart pump according to claim 2, wherein the impeller is a rotary impeller and comprises a propeller shaft disposed in the housing.

4. The heart pump according to claim 2, wherein the impeller is a rotary impeller and comprises an Archimedes screw or worm shaft disposed in the housing.

5. The heart pump according to claim 1, wherein the impeller is a rotary impeller and comprises a propeller shaft disposed in the housing.

6. The heart pump according to claim 1, wherein the impeller is a rotary impeller and comprises an Archimedes screw or worm shaft disposed in the housing.

7. The heart pump according to claim 1, wherein the housing is a longilinear cylinder, a side wall of which is perforated to enable a discharge of drawn blood, and an axis of rotation of which is facing corresponding sigmoid valves.

8. The heart pump according to claim 1, wherein the management unit is biocompatible and is configured to be positioned inside the patient in an epigastric region.

9. The heart pump according to claim 1, wherein at least the motor is removable.

10. The heart pump according to claim 1, wherein the power supply comprises at least one rechargeable battery.

11. The heart pump according to claim 1, further comprising an activity sensor configured to collect cardiac activity to synchronize an operation of the impeller with electrosystolic activity of the heart, the activity sensor being configured to be connected to the wall of the heart and having a wired link to the management unit.

12. The heart pump according to claim 1, further comprising a cardiac activity collection and stimulation sensor configured to be connected to a wall of the systemic ventricle and configured to communicate with the management unit.

13. The heart pump according to claim 1, further comprising a cardiac activity collection and stimulation non-systemic sensor configured to be connected to a wall of the non-systemic ventricle and configured to communicate with the management unit.

14. The heart pump according to claim 1, further comprising a cardiac activity collection and stimulation atrium sensor configured to be connected to a wall of a systemic atrium and configured to communicate with the management unit.

15. The heart pump according to claim 1, further comprising a cardiac activity collection, stimulation and defibrillation sensor configured to be connected to the wall of the heart and having a wired link to the management unit, wherein the control unit is configured as a defibrillator.

16. The heart pump according to claim 1, wherein the management unit has a wireless link to a defibrillator.

17. The heart pump according to claim 1, further comprising a second impeller configured to be positioned on a non-systemic ventricle and linked to said management unit.

18. A method of regulating blood flow in a heart by a heart pump, the method comprising:
    providing a heart pump configured to be attached to the heart and configured to be inserted partly into a systemic ventricle of the heart, through a wall of the heart, the heart pump comprising:
        a housing configured to be positioned inside the systemic ventricle to draw up blood inside the systemic ventricle and to discharge the blood inside the systemic ventricle and through sigmoid valves of the systemic ventricle,
        an impeller configured to be inserted inside the housing,
        a motor connected to the housing,
        a sealing and fixing membrane fastened to and around the motor and configured to secure the heart pump to the wall of the heart and to partly arrange the motor outside the systemic ventricle,
        a management unit comprising a power supply, and an impeller control unit, and
        a wired link between the management unit and the impeller; and
    controlling a speed and an operating time of the pump in order to regulate blood flow when the heart pump is attached to the heart based on predetermined control laws or based on an automatic control instruction relating to cardiac activity.

19. The method according to claim 18, wherein, when the speed and the operating time of the pump are controlled based on the automatic control instruction, the automatic control instruction is developed by collecting cardiac activity by a sensor configured to be connected to the wall of the heart and having a wired link to the management unit.

20. The method according to claim 18, wherein at least at least one stimulation sensor is configured to be connected to the wall of the heart and is configured to stimulate the heart to regulate blood flow, the at least one stimulation sensor having a wired link to the management unit.

* * * * *